United States Patent [19]
Snow et al.

[11] Patent Number: 5,817,292
[45] Date of Patent: *Oct. 6, 1998

[54] MR IMAGING COMPOSITIONS AND METHODS

[75] Inventors: Robert A. Snow, West Chester; David L. Ladd, Wayne; John L. Toner, Downingtown, all of Pa.

[73] Assignee: Nycomed Imaging AS, Norway

[*] Notice: The term of this patent shall not extend beyond the expiration date of Pat. No. 5,583,206.

[21] Appl. No.: 960,746

[22] Filed: Oct. 14, 1992

[51] Int. Cl.$^6$ .................................................. A61K 49/00
[52] U.S. Cl. ................. 424/9.323; 424/9.34; 424/9.361; 424/9.364; 534/10; 534/15; 534/16; 540/452; 540/465; 546/5; 556/40; 556/50; 556/63; 556/116; 556/148
[58] Field of Search ................................. 534/10, 15, 16; 540/452, 465; 546/5; 556/40, 50, 63, 116, 148; 424/9.323, 9.34, 9.361, 9.364

[56] References Cited

U.S. PATENT DOCUMENTS

| | | | |
|---|---|---|---|
| 4,407,978 | 10/1983 | Kahovec et al. | 521/56 |
| 4,556,689 | 12/1985 | Murakami et al. | 525/54.1 |
| 4,602,097 | 7/1986 | Curtis | 549/27 |
| 4,615,879 | 10/1986 | Runge et al. | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,746,507 | 5/1988 | Quag | 424/9 |
| 4,804,529 | 2/1989 | Bardy et al. | 424/9 |
| 4,814,098 | 3/1989 | Inada et al. | 252/62.51 |
| 4,822,594 | 4/1989 | Gibby | 424/9 |
| 4,826,673 | 5/1989 | Dean et al. | 424/9 |
| 4,859,451 | 8/1989 | Quay et al. | 424/9 |
| 4,909,257 | 3/1990 | Engelstad et al. | 128/654 |
| 4,916,246 | 4/1990 | Felder et al. | 556/1 |
| 4,933,441 | 6/1990 | Gibby | 536/112 |
| 4,943,523 | 7/1990 | Stavrianopoulos | 435/7 |
| 4,963,344 | 10/1990 | Gries et al. | 424/9 |
| 4,972,837 | 11/1990 | Engelstad et al. | 128/654 |
| 4,980,148 | 12/1990 | Dean | 424/9 |
| 4,980,502 | 12/1990 | Felder et al. | 562/444 |
| 4,985,233 | 1/1991 | Klaveness et al. | 424/9 |
| 4,986,980 | 1/1991 | Jacobsen | 424/9 |
| 5,057,302 | 10/1991 | Johnson et al. | 424/1.1 |
| 5,077,037 | 12/1991 | Wallace | 424/9 |
| 5,130,120 | 7/1992 | Weber . | |
| 5,137,711 | 8/1992 | Weber . | |
| 5,208,324 | 5/1993 | Klaveness et al. | 534/16 |
| 5,358,702 | 10/1994 | Unger . | |
| 5,368,840 | 11/1994 | Unger . | |
| 5,385,719 | 1/1995 | Unger et al. | 528/272 |
| 5,407,657 | 4/1995 | Unger et al. | 424/9 |
| 5,458,127 | 10/1995 | Unger et al. | 128/653.4 |

FOREIGN PATENT DOCUMENTS

| | | |
|---|---|---|
| 0200467 | 11/1986 | European Pat. Off. . |
| 0 326 226 | 8/1989 | European Pat. Off. . |
| 0430863 | 6/1991 | European Pat. Off. . |
| 0466200 | 1/1992 | European Pat. Off. . |
| 0450742 | 10/1992 | European Pat. Off. . |
| WO 85 05554 | 12/1985 | WIPO . |
| 9004384 | 10/1988 | WIPO . |
| 9001024 | 2/1990 | WIPO . |
| 9115753 | 10/1991 | WIPO . |
| 9118630 | 12/1991 | WIPO . |
| WO93/06148 | 4/1993 | WIPO . |

OTHER PUBLICATIONS

H. Frank et al., "High Resolution 3–D MR Angiography of Pulmonary Vessels in an Animal Model", XVth Congress of the European Society of Cardiology, Nice, France, Aug. 29–Sep. 2, 1993, p. 188.

G.K. Von Schulthess et al., "Polyethelene–glycol–ferrioxamine. A New Magnetic Resonance Contrast Agent", Invest. Radiol., US, 1990, vol. 25, Suppl. 1, p. S48.

Makrlik, Emanuel, "Hydration of Complexes of Some Univalent Cations with Polyethylene Glycol Ligands in Nitrobenzene Saturated with Water", Collect. Czech. Chem. Commun., vol. 57, pp. 289–295.

S. Duewell et al., "Nonionic Polyethylene Glycol–Ferrioxamine as a Renal Magnetic Resonance Contrast agent", Invest Radiol., Jan. 1991, vol. 26, No. 1, pp. 50–57.

HG Botros et al., "Immobilized Metal Ion Affinity Partioning of Cells in Aqueous Two–Phase Systems; Erythrocytes as a Model", Biochim Biophys Acta, 24 May 1991, vol. 1074, No. 1, pp. 79–73.

A. Otto et al., "Recognition and Separation of Isoenzymes by Metal Chelates. Immobilized Metal Ion Affinity Partitioning of Lactate Dehydrogenase Isoenzymes", J. Chromatogr, NL, Jul. 30, 1993, vol. 644 pp. 25–33.

A.A. Bogdanov, Jr., et al., "A New Macromolecule as a Contrast Agent for MR Angiography: Preparation, Properties, and Animal Studies", Radiology, US, Jun. 1993, vol. 187,No. 3, pp. 701–706.

V. Molak et al., "Dystrophic Mouse Muscles Have Leaky Cell Membranes", Exp. Neurol, vol. 70, No. 2, pp. 452–457, 1980.

Werner Mueller et al., "Polyethylene Glycol Derivatives of Base and Sequence Specific DNA Ligands: DNA Interaction and Appln for Base Specific Separation of DNA . . . ", Nucleic Acids Res, 1981, 9, 95–119.

Yokoyama et al, "Molecular Design For Missile Drug . . . " Makromol. Chem. 190, 2041–2054 (1989).

Schunmann—Giampieri et al, "in vivo and in vitro Evaluation of Gd–DTPA–Polylysine . . . " Invesigative Radiology, 969–974 (1991).

Marchal et al, "MR Angiography with Gadopentetate . . . " AJR:155, 407–411 (1990).

Mutter, "Soluble Polymers in Organic Synthesis: I. Preparation of Polymer Reagents . . . " Tetrahedron Letters, 31, (1978) 2839–42.

Harris et al, "Synthesis & Characterization of Poly(ethylene Glycol) Derivatives". J. of Poly. Science, 22, 341–352 (1984).

Shen et al, "Copolymeric MR Contrast Agents", J. Mag. Res. IM., 2, 115 (1992).

Primary Examiner—Richard L. Raymond
Attorney, Agent, or Firm—Fish & Richardson P.C.

[57] ABSTRACT

This invention provides compositions useful in MR imaging comprising a polymer comprising units comprising the residue of a chelating agent linked to a poly(alkylene oxide) moiety, the polymer having a paramagetic metal ion associated therewith.

15 Claims, 3 Drawing Sheets

MR IMAGING COMPOSITIONS AND METHODS

CROSS REFERENCE TO RELATED APPLICATIONS

Reference is hereby made to commonly assigned copending U.S. patent application Ser. No. 08/348,197 (which is a continuation of U.S. patent application Ser. No. 07/961,146 filed Oct. 14, 1992, now abandoned) entitled Chelating Polymers and U.S. patent application Ser. No. 08/493,523 (which is a continuation of Ser. No. 08/352,682 filed Dec. 30, 1994, now abandoned, which is a continuation of Ser. No. 07/960,745 filed Oct. 14, 1992, now abandoned) entitled Therapeutic and Diagnostic Imaging Compositions and Methods filed concurrently herewith.

FIELD OF INVENTION

This invention relates to chelating polymers useful as magnetic resonance (MR) contrast agents for use in MR imaging compositions and methods.

BACKGROUND OF THE INVENTION

Magnetic resonance (MR) is widely used for obtaining spatial images of human and mammalian subjects for clinical diagnosis. A review of this technology and clinical applications is provided by D. P. Swanson et al, in Pharmaceuticals in Medical Imaging, 1990, Macmillan Publishing Company, pages 645–681.

MR images are derived as a composite of the effects of a number of parameters which are analyzed and combined by computer. Choice of the appropriate instrument parameters, such as radio frequency (Rf), pulsation and timing can be utilized to enhance or attenuate the signals of any of the image-producing parameters to thereby improve image quality and provide better anatomical and functional information. In many cases, MR imaging has proven to be a valuable diagnostic tool, inasmuch as normal and diseased tissue, by virtue of their possessing different parameter values, can be differentiated in the image.

In MR imaging, the in vivo image of an organ or tissue is obtained by placing the body of a subject in a strong external magnetic field, pulsing with radio frequency energy, and observing the effect of the pulses on the magnetic properties of the protons contained in and surrounding the organ or tissue. A number of parameters can be measured. The proton relaxation times, $T_1$ and $T_2$, are of primary importance. $T_1$, also called the spin-lattice or longitudinal relaxation time, and $T_2$, also called the spin—spin or transverse relaxation time, are functions of the chemical and physical environment of the organ or tissue water and are measured using Rf pulsing techniques. This information is analyzed as a function of spatial location by computer which transforms the information to generate an image.

Often the image produced lacks appropriate contrast, e.g., between normal and diseased tissue, reducing diagnostic effectiveness. To overcome this drawback, contrast agents have been used. Contrast agents are substances which exert an effect on the MR parameters of various chemical species proximal them. Theoretically, a contrast agent, if taken up preferentially by a certain portion of an organ or a certain type of tissue, e.g., diseased tissue, can provide contrast enhancement in the resultant images.

Inasmuch as MR images are strongly affected by variations in the $T_1$ and $T_2$ parameters, it is desirable to have a contrast agent which effects either or both parameters. Research has focused predominantly on two classes of magnetically active materials, i.e., paramagnetic materials, which act primarily to decrease $T_1$, and superparamagnetic materials, which act primarily to decrease $T_2$.

Paramagnetism occurs in materials that contain unpaired electrons. Paramagnetic materials are characterized by a weak magnetic susceptibility (response to an applied magnetic field). Paramagnetic materials become weakly magnetic in the presence of a magnetic field and rapidly lose such activity, i.e., demagnetize, once the external field has been removed. It has long been recognized that the addition of paramagnetic solutes to water causes a decrease in the $T_1$ parameter.

Paramagnetic materials, for example, Gd containing materials, have been used as MR contrast agents primarily because of their effect on $T_1$. Gd has the largest number of unpaired electrons (seven) in its 4f orbitals and exhibits the greatest longitudinal relaxivity of any element.

A major concern with the use of contrast agents for MR imaging is that many paramagnetic materials exert toxic effects on biological systems making them inappropriate for in vivo use. For example, the free solubilized form of Gd salts are quite toxic. To make gadolinium ion more suitable for in vivo use, researchers have chelated it with diethylenetriaminepentaacetic acid (DTPA). A formulation of this material that has undergone extensive clinical testing consists of Gd-DTPA neutralized with two equivalents of N-methyl-D-glucamine (meglumine). This agent has been successful in enhancing human brain and renal tumors.

Despite its satisfactory relaxivity and safety, this formulation has several disadvantages. For example, due to its low molecular weight, Gd-DTPA dimeglumine is cleared very rapidly from the blood stream and tissue lesions (tumors). This limits the imaging window, the number of optimal images that can be taken after each injection, and increases the agents required dose and relative toxicity. In addition, the biodistribution of Gd-DTPA is suboptimal for imaging body tumors and infections due to its small molecular size.

Several approaches have been taken in attempts to overcome these disadvantages. For example, Gd and Gd-chelates have been chemically conjugated to macromolecular proteins such as albumin, polylysines and immunoglobulins. Drawbacks of conjugating DTPA to protein carriers for use in MR image enhancement include inappropriate biodistribution and toxicity. In addition, proteins provide a defined platform not subject to wide synthetic variation. Additionally, thermal sterilization of protein conjugates tends to be problematic, especially in the case of albumin conjugates.

Thus, it is readily apparent that it would be highly desirable to provide easily produced MR contrast agents which contain relatively large amounts of metal per molecule, i.e., are of high substitution ratios, yet are of a molecular weight enabling them to be circulated within the blood pool for extended periods of time, and/or which exhibit improved biodistribution for imaging blood vessels, body tumors and other tissues.

SUMMARY OF THE INVENTION

We have discovered that reactive poly(alkylene oxides) can be contacted with chelating agents or precursors thereof containing reactive functionality to form metallizeable polymers which when associated with paramagnetic metal ions provide polymeric chelates of extraordinary utility as contrast agents for MR imaging.

More particularly, in accordance with this invention, there is provided a polymer, suitable for use as a contrast agent for MR imaging, containing units comprising the residue of a chelating agent linked to a poly(alkylene oxide) moiety, such polymer having a paramagnetic metal ion associated therewith. The polymer preferably comprises units having the structure I:

wherein:

Z is the residue of a chelating agent;

Q is a poly(alkylene oxide) moiety;

L and $L_1$ independently represent a chemical bond or a linking group;

$M^{(+a)}$ is one or more cations, at least one of which is a paramagnetic ion and having a total charge of +a;

$E^{(b)}$ is one or more counterions having a total charge of b;

w is 0 or 1;

r is 0 or 1;

d is the total charge on the linked residue of the chelating group; and a=d+b.

This invention further provides a method of performing an MR diagnostic procedure in a body comprising administering to the body a contrast enhancing amount of the polymer described above, and then exposing the body to an MR measurement step to image at least a portion of the body.

It is a particularly advantageous feature that the paramagnetic polymeric chelates of this invention provide effective MR contrast enhancement of the blood pool within the vascular system for remarkably long periods of time.

It is an advantageous feature of this invention that polymeric compounds are provided having a specificity toward accumulation in different tissues, for example, in tumors and the liver.

It is another advantageous feature of this invention that polymeric chelates suitable for MR imaging are provided containing relatively large amounts of metal, which chelates are potentially more stable in vivo and less immunoreactive than protein-chelate-metal complexes.

Yet another advantageous feature of this invention is that the molecular weight of the above-described polymers can be synthetically tailored to produce an agent of desired composition, molecular weight and size.

Still other advantageous features of this invention will become readily apparent upon reference to the following description of preferred embodiments.

DESCRIPTION OF PREFERRED EMBODIMENTS

While the polymer of this invention is described herein primarily in connection with its preferred utilities, i.e., as a contrast agent for use in MR imaging compositions and methods, it also finds utility in other applications and fields, e.g., as a therapeutic agent and as an additive for paints, coatings and adhesives and as an antistatic agent for use in photographic and magnetic recording elements.

The polymer useful in the practice of the invention contains units comprising the residue of a chelating agent linked to a poly(alkylene oxide) moiety in the backbone of the polymer chain. The polymer comprises from 2 to 1000 or more, preferably 3 to 1000, of the above described units. In preferred embodiments, the above-described units are recurring units.

In formula I above, Q represents a linear or branched poly(alkylene oxide) moiety. Exemplary poly(alkylene oxide) moieties include poly(ethylene oxides), poly (propylene oxides) and poly(butylene oxides). Preferred poly(alkylene oxides) include poly(ethylene oxides) (PEO), poly(propylene oxides) (PPO) and random and block copolymers of PEO and PPO. PEO containing polymers are particularly preferred when it is desired for the final polymer to possess solubility in water. It is also contemplated that the poly(alkylene oxide) moiety can comprise glycerol poly (alkylene oxide) triethers, polyglycidols, linear, block and graft copolymers of alkylene oxides with compatible comonomers such as poly(ethyleneimine-co-ethylene oxide), and grafted block copolymers such as poly(methyl vinyl ether-co-ethylene oxide). For MR imaging applications, preferred poly(alkylene oxide) moieties have an average molecular weight in the range from about 100–20,000, more preferably 250–10,000 daltons. These moieties can be derived from poly(alkylene oxide) moieties which are commercially available in the corresponding diol form and/or can be prepared by techniques well known to those skilled in the art. A particularly preferred class of PEO moieties derived from PEGs can be represented by the structure:

wherein m is 1 to 500, preferably 1 to 250, and more preferably 1 to 100.

The polymer of the invention can comprise the residue of one or more of a wide variety of chelating agents. As is well known, a chelating agent is a compound containing donor atoms that can combine by coordinate bonding with a cation to form a cyclic structure called a chelation complex or chelate. This class of compounds is described in the Kirk-Othmer Encyclopedia of Chemical Technology, Vol. 5, 339–368.

The residues of suitable chelating agents can be derived from and selected to contain chelating elements selected from polyphosphates, such as sodium tripolyphosphate and hexametaphosphoric acid;

aminocarboxylic acids, such as ethylenediaminetetraacetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentacetic acid;

1,3-diketones, such as acetylacetone, trifluoroacetylacetone, and thenoyltrifluoroacetone;

hydroxycarboxylic acids, such as tartaric acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxine-sulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids;

Schiff bases, such as disalicylaldehyde 1,2-propylenediimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18]crown-6, $(CH_3)_6$-[14]-4,11-diene-$N_4$, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred residues of chelating agents contain polycarboxylic acid or carboxylate groups and include elements present in: ethylenediamine-N, N, N',N'-tetraacetic acid (EDTA); N,N,N',N",N"-diethylenetriaminepentaacetic acid (DTPA); 1,4,7,10-tetraazacyclododecane-N,N',N",N"'-tetraacetic acid (DOTA); 1,4,7,10-tetraazacyclododecane-N, N',N"-triacetic acid (DO3A); 1-oxa-4,7,10-triazacyclododecane-N,N',N"-triacetic acid (OTTA); trans (1,2)-cyclohexanodiethylenetriamine pentaacetic acid (CDTPA);

(B4A);

(P4A);

(TMT);

(DCDTPA); and

(PheMT).

Other suitable chelating groups are described in PCT/US91/08253, the disclosure of which is hereby incorporated by reference. In formula I above, Z is the residue of one or more chelating agents. If Z is the residue of multiple chelating units, such units can be linked together by a linking group such as described below.

The residue of the chelating agent is linked to the poly (alkylene oxide) moiety through a chemical bond or a linking group, i.e., L and $L_1$ in formula I above. Preferred linking groups include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups;

carbonyl;
sulfonyl;
sulfinyl;
ether;
thioether;
ester, i.e., carbonyloxy and oxycarbonyl;
thioester, i.e., carbonylthio, thiocarbonyl, thiocarbonyloxy and oxythiocarbonyl;
amide, i.e., iminocarbonyl and carbonylimino;
thioamide, i.e., iminothiocarbonyl and thiocarbonylimino;

thio;
dithio;
phosphate;
phosphonate;
urelene;
thiourelene;
urethane, i.e., iminocarbonyloxy and oxycarbonylimino;
thiourethane, i.e., iminothiocarbonyloxy, and oxythiocarbonylimino;
an amino acid linkage, i.e., a group wherein n=1 and $X^1$, $X^2$ and $X^3$ independently are H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e., a group wherein n>1 and each $X^1$, $X^2$ and $X^3$ are independently represented by a group as described for $X^1$, $X^2$ and $X^3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry. Especially preferred linking groups include unsubstituted or substituted imino groups which when linked to the carbonyl in the residue of a chelating agent forms an amide group.

The linking groups can contain various substituents which do not interfere with the polymerization reaction. The linking groups can also contain substituents which can otherwise interfere with the polymerization reaction, but which during the polymerization reaction, are prevented from so doing with suitable protecting groups commonly known in the art and which substituents are regenerated after the polymerization by suitable deprotection. The linking groups can also contain substituents that are introduced after the polymerization. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; the residue of a chelating group, preferably comprised of elements such as described for Z above but being subtended from the backbone at one covalent site of such elements; or a poly(alkylene oxide) moiety, preferably such as described for Q above but being subtended from the backbone of the polymer at one site of the poly(alkylene oxide) moiety and terminated by substituents selected from, for example, H, OH, alkyl, alkoxy, or elements of a chelating agent as described above.

In a preferred embodiment, L and $L_1$, represent wherein $L_2$ and $L_3$ independently represent a chemical bond or a linking group such as described above, and R and $R^1$ independently represent H; or a substituent attached to the linking group such as described above.

E can be one or more counterions. For example, E can be one or more anions, such as a halide, such as chloride and iodide; sulfate; phosphate; nitrate; and acetate. E can be one or more cations such as $Na^+$, $K^+$, meglumine, and the like. For in vivo applications, nontoxic physiologically tolerable anions are, of course, desirable.

For MR imaging applications, $M^{(+a)}$ preferably represents a paramagnetic metal ion such as an ion of metals of atomic number 21 to 29, 42, 44 and 57 to 71, especially 57 to 71. Ions of the following metals are preferred: Cr, V, Mn, Fe, Co, Ni, Cu, La, Ce, Pr, Nd, Pm, Sm, Eu, Gd, Tb, Dy, Ho, Er, Tm, Yb and Lu. Especially preferred are $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$. As noted, it is a particularly advantageous feature that polymers are provided exhibiting a high substitution ratio, i.e., containing relatively large numbers of paramagnetic metal ions per molecule.

In the structure above, w is 0 or 1, r is 0 or 1, a is an integer preferably from 1 to 4, b is an integer preferably from 0 to 3, and d is an integer preferably from 0 to 4. When E is present, i.e., when w is 1, b most preferably is 1 or 2. When Z is the residue of multiple chelating groups, d can range up to about 100. The total positive charge on the cations equals the sum of the total charge on the residue of the chelating group plus the total charge on any counterions E present, i.e., a=d+b.

The metal content in the polymer can vary from about 0.1 up to about 30% based on the total weight of the polymer. For MR imaging, the polymer preferably contains the paramagnetic metal in an amount of from 1 to 25%, more preferably 2–20% by weight.

For MR imaging, the polymer preferably comprises from 2 to about 100, more preferably 2 to 10 recurring units. If the polymer contains a peptide that can be hydrolyzed, then the polymer can contain from 1 to several hundred paramagnetic metal ions per molecule.

The polymer in structure I can be capped at the termini with groups independently selected from Z, Q, L or $L_1$ to which is bound a terminal hydrogen atom, OH, alkyl, alkoxy, or elements of a linking group substituent such as described above. In preferred embodiments, wherein the polymer is a polyamide, the polymer can be capped with groups such as hydrogen or hydroxyl groups or with groups derived from polyamide chain terminating agents such as from monoamines and monoacyl derivatives such as monoanhydrides, e.g., acetic anhydride, or with groups derived from the elements of the residue of a chelating group as defined above. It is further contemplated that cyclic polymers, i.e., non-capped polymers can be prepared.

The polymer of this invention can be prepared in water-soluble, water-dispersible or water-insoluble forms depending upon the intended application. The polymer can be crosslinked or non-crosslinked. The molecular weight of the polymer can vary widely, i.e., from about 1,000 to $10^8$ or greater, as measured by gel permeation chromatography (GPC). The water-soluble polymer preferably is of molecular weight from 1,000 to about 250,000. The water-insoluble crosslinked polymer can be of molecular weight from about $10^5$ to $10^7$ or greater. For MR imaging, the polymer preferably is of molecular weight 5,000 to $10^6$, more preferably 10,000 to 100,000.

The polymer of this invention can be prepared by contacting a reactive poly(alkylene oxide) species with a chelating agent or precursor thereof containing reactive functionality in a non-reactive solvent to form the polymer. The poly(alkylene oxide) can be substituted or unsubstituted.

The preferred reaction conditions, e.g., temperature, pressure, solvent, etc., depend primarily on the particular reactants selected and can be readily determined by one skilled in the art.

Suitable reactive poly(alkylene oxide) species include terminally functionalized poly(alkylene oxide) diamines, poly(alkylene oxide) dihydrazines, poly(alkylene oxide) diisocyantes, poly(alkylene oxide) diols, poly(alkylene oxide) dialdehydes, poly(alkylene oxide) dicarboxylic acids, poly(alkylene oxide) bis(vinyl sulfonyl) ethers, poly(alkylene oxide) diphosphates, poly(alkylene oxide) N,N-dialkylaminophosphoramidates, poly(alkylene oxide) diepoxides, poly(alkylene oxide) dialkoxides, poly(alkylene oxide) disulfonates, poly(alkylene oxide) dihalides and the like. The above-described poly(alkylene oxide) species are linear difunctional species. Tri- and higher multifunctional branched species relating to the above are also useful.

Suitable chelating agents and precursors thereof containing reactive functionality include polycarboxylic acids in dianhydride form, di(sulfonyl chlorides), di(alkyl sulfates), di(vinyl sulfones), diesters, and the like. As will be recognized by one skilled in the art, a suitably blocked pregenitor to the chelating agent or precursor thereof containing reactive functionality can be contacted with the reactive poly(alkylene oxide) moiety to form the polymer, and then the blocking group can be subsequently removed by techniques known in the art. It is contemplated that additional chelating functional groups can be introduced by suitable chemical modification at the unblocked sites. If hydroxy substituents are to be selectively present in the final polymer, they preferably should be temporarily blocked during polymerization, e.g., by conventional blocking techniques to minimize formation of undesirable byproducts, e.g., polyester-amide derived therefrom. However, for some purposes, polyester-polyamides which contain one or more ester linking groups in the backbone of the polymer are contemplated to be useful. The use of condensing agents such as carbodiimides is also contemplated to be useful in the formation of the polymers of this invention.

In a preferred embodiment, the polymer of this invention can be prepared by reacting a linear poly(alkylene oxide) diamine with a precursor of a chelating agent in an internal dianhydride form.

The poly(alkylene oxide) diamine can be prepared by reacting an activated form of the poly(alkylene oxide) with ammonia, a primary amine, a polyamine, an amide or an azide followed by reduction. The amino group can be introduced by other methods known in the art. Suitable illustrative amines include N-methylamine, amino acids, aminomethyl pyridine, aminomethylthiophene, methoxyethoxyethylamine, methoxyethylamine and aminobenzoic acid. Exemplary useful polyamines include diaminohexane, tris(aminoethyl)amine, and diethylenetriamine.

The linear poly(alkylene oxide) in its diol form is widely available commercially or can be prepared by techniques well known to those skilled in the art. The poly(alkylene oxide) is activated for nucleophilic displacement by reacting it with an activator such as p-toluenesulfonyl chloride, thionyl chloride, thionyl bromide, an alkylsulfonyl chloride, e.g., $CH_3SO_2Cl$, a sulfonic acid anhydride, or any other suitable activator known in the art. The activated form of the poly(alkylene oxide) thus can be a ditosylate, a dichloride, a dibromide, etc.

The activated form of the poly(alkylene oxide) is reacted preferably with a stoichiometric excess of the amine, in an inert solvent preferably at a temperature, e.g., 100°–160° C., and pressure, e.g., 1 to 10 atmospheres, sufficient to drive the reaction to completion. Suitable solvents include dioxane, ethanol, and other alcohols. Thereafter, the poly(alkylene oxide) diamine preferably is isolated, e.g., by evaporation or precipitation, and purified, e.g., by dissolving in a suitable solvent such as methylene chloride, chloroform or trichloroethane, and then washing the solution with an excess of aqueous NaOH, or by any other suitable isolation and purification techniques.

The internal anhydride forms of the chelating agents described above are commercially available and/or can be prepared by techniques known in the art. For example, the internal anhydride forms of EDTA and DTPA are commercially available. The internal anhydride forms of DOTA, DO3A, OTTA, B4A, P4A and TMT can be prepared by techniques known in the art. For example, the anhydrides can be prepared by heating the corresponding acids in acetic anhydride in the presence of pyridine as catalyst. Methods for the preparation of B4A, P4A and TMT are described in U.S. Pat. No. 4,859,777. Mixed anhydrides are also suitable.

The reactive poly(alkylene oxide) diamine can be reacted with the internal dianhydride in a non-reactive solvent to form the unmetallized polymer. The reaction conveniently can take place at approximately room temperature and atmospheric pressure. However, higher and lower temperatures and pressures are contemplated. Suitable solvents include dimethylsulfoxide, dimethylformamide, acetonitrile, chloroform, dichloromethane and 1,2-dichloroethane. The nonmetallized polymer preferably is isolated and then purified, e.g., by diafiltration.

The metallized polymer can be formed by contacting the unmetallized polymer sequentially or simultaneously with one or more sources of metal ions. This can be conveniently accomplished by adding one or more metal ion solutions or one or more metal ion solid salts or metal ion oxides, preferably sequentially, to a solution, preferably an aqueous solution, of the polymer. Thereafter, or between sequential addition of metal ions, the chelated polymer preferably is diafiltered in water to remove excess unbound metal.

A general reaction scheme for this method of preparing the polymers of this invention and illustrative examples are set forth below.

Alternatively, the polymer can be prepared in a condensation polymerization reaction between a suitable diamine and a diacid containing the metallized chelating group, in a suitably activated form, e.g., in the form of an activated diester.

The molecular weight of the polymer product depends upon many factors including, for example, the molecular weight of the starting poly(alkylene oxide) moiety, the presence or absence of reactive polymerization chain terminating agents such as monoanhydrides or monoamines in the case of polyamides which reduce molecular weight by end-capping the polymer during the polymerization process, the presence or absence of reactive crosslinkers or low molecular weight chain extenders which increase the molecular weight of the polymer during polymerization, and the relative concentrations of the poly(alkylene oxide) and chelator moiety present during the polymerization reaction which in turn affects the number of recurring units in the polymer product. To form the polymer of this invention in a water-insoluble form, the above described procedure can be modified to incorporate a crosslinkable tri- or higher polyamine, and/or by adding a reactive crosslinking agent, which can be the reactive chelating moiety, or, e.g., a diacid or higher acid chloride, to the polymerization reaction. The preparation of insoluble and water-soluble polymers of molecular weight 1,000 to $10^8$ can be accomplished by routine experimentation by one skilled in the art of polymer synthesis techniques.

The polymer preferably is prepared in a water soluble, i.e., injectable form when used as an MR contrast agent for blood pool imaging or as a composition intended to be administered intravenously. On the other hand, the polymer can be prepared preferably as a water-insoluble polymer when intended to be administered orally as an MR contrast agent for gastro-intestinal imaging.

The dosages of the contrast agent used according to the method of the present invention will vary according to the precise nature of the contrast agent used. Preferably however, the dosage should be kept as low as is consistent with achieving contrast enhanced imaging and volumes minimized for IV drip or bolus injection. In this way, the toxicity potential is minimized. For most MR contrast agents the appropriate dosage will generally range from 0.02 to 3 mmol paramagnetic metal/kg body weight, especially 0.05 to 1.5 mmol/kg, particularly 0.08 to 0.5, more especially 0.1 to 0.4 mmol/kg. It is well within the skill of the average practitioner in this field to determine the optimum dosage for any particular MR contrast agent by relatively routine experimentation, for both in vivo or in vitro applications.

Contrast agents may be formulated with conventional pharmaceutical or veterinary aids, for example stabilizers, antioxidants, osmolality adjusting agents, buffers, pH adjusting agents, etc., and may be in a form suitable for injection or infusion directly or after dispersion in or dilution with a physiologically acceptable carrier medium, e.g., water for injection. Thus the contrast agents may be formulated in conventional administration forms such as powders, solutions, suspensions, dispersions, etc., however solutions, suspensions and dispersions in physiologically acceptable carrier media will generally be preferred.

The contrast agents may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g., intravenous solutions, should of course be sterile and free from physiologically unacceptable agents, and should have low osmolality to minimize irritation or other adverse effects upon administration. Thus, the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

The following examples further illustrate the invention.

Examples 1–12 illustrate the preparation of non-crosslinked polymers of the invention.

EXAMPLE 1

A polymer of the invention (Ia) was prepared in accordance with reaction scheme A as described below.

Scheme A

A solution of 100.0 g (0.0690 mol) of PEO of average molecular weight (MW) 1450 in toluene (1500 ml) was refluxed for 2 hours with azeotropic removal of water. The solution was cooled to 25° C., then treated with triethylamine (46.1 ml, 0.331 mol), 4-dimethylaminopyridine (1.69 g, 0.0138 mol) and p-toluenesulfonyl chloride (57.9 g, 0.303 mol), and then heated for 4 days at 60° C. under an atmosphere of nitrogen. After cooling to room temperature, the reaction mixture was filtered and the filtrate was extracted twice with water. The combined aqueous extracts were washed with ether, then extracted twice with $CHCl_3$. The combined $CHCl_3$ extracts were dried over anhydrous magnesium sulfate and then concentrated to yield 121.3 g of product (1).

A solution of 42.2 g (0.0240 mol) of the ditosylate 1 in 420 ml of dioxane was cooled in an ice bath and a stream of methylamine was introduced over a period of 35 minutes. The reaction mixture was then heated in a sealed stainless steel reactor at 160° C. for 16 hours, cooled to room temperature, and then filtered. The filtrate was concentrated to remove solvent, then treated with water (844 ml) and 1.0N NaOH (95.2 ml) and extracted twice with $CHCl_3$. The combined $CHCl_3$ extracts were dried over anhydrous magnesium sulfate and concentrated to leave 31.0 g of product (2) ($R^2=CH_3$).

A solution of 9.00 g (6.10 mmol) of the bis-(N-methylamine) 2 in 45 mls of dimethylsulfoxide (DMSO) was treated with triethylamine (1.70 ml, 12.2 mmol) and a solution of 2.18 g (6.10 mmol) of diethylenetriaminepentaacetic acid internal dianhydride in DMSO (45 mls). The reaction mixture was stirred at room temperature for 16 hours, then treated with 360 ml of water. The resultant solution was filtered through a 0.45 μm nylon filter and the filtrate was diafiltered against water in a diafiltration cell equipped with a 3000 MW cut-off membrane to leave 170 ml of a solution of (3) ($R^2=CH_3$).

A 160 ml portion of the aqueous solution was treated with a two-fold molar excess of gadolinium(III) chloride hexahydrate, and then was diafiltered against water as described above. Lyophilization of the retentate yielded 8.66 g of product (Ia) ($R^2=CH_3$) of average MW 16,300 daltons (as determined by SEC-HPLC using PEO molecular weight standards). Elemental analysis for $C_{82}H_{156}GdN_5O_{40} \cdot 4H_2O$:

| Element | % Theory | % Found |
|---------|----------|---------|
| C       | 47.32    | 47.15   |
| H       | 7.94     | 7.89    |
| N       | 3.36     | 3.30    |
| Gd      | 7.55     | 7.37    |

The relaxivity $(T_1)^{-1}$ of this material at 20 MHz and 40° C. was found to be 6.2 $mM^{-1}s^{-1}$.

Intravenous administration of 100, 200 and 400 mg/Kg to mice resulted in no deaths, no effect on body weight and no abnormalities upon necropsy after 14 days.

The same product, but prepared using radioactive $^{153}$Gd was employed in biodistribution studies in rats to determine a blood-pool half-life (elimination phase) of 75 minutes.

EXAMPLE 2

In a manner similar to Example 1, a polymeric gadolinium chelate (Ia, $R^2=CH_3$) of average MW 8,010 was prepared from PEO of MW 1000. The blood-pool half-life (elimination phase) was determined to be 48 minutes.

EXAMPLE 3

In a manner similar to Example 1, a polymeric gadolinium chelate (Ia, $R^2=CH_3$) of average MW 16,800 was prepared from PEO of average MW 2000.

EXAMPLE 4

In a manner similar to Example 1, a polymeric gadolinium chelate (Ia, $R^2=CH_3$) of average MW 22,400 was prepared from PEO of average MW 3350. Elemental analysis for $C_{168}H_{328}GdN_5O_{83} \cdot 5H_2O$:

| Element | % Theory | % Found |
|---------|----------|---------|
| C       | 50.00    | 50.00   |
| H       | 8.53     | 8.61    |
| N       | 1.75     | 1.71    |
| Gd      | 3.94     | 3.78    |

The blood-pool half-life (elimination phase) of this material in rats was determined to be 141 minutes.

EXAMPLE 5

This example describes the preparation of a polymer (Ia) wherein $R^2=H$.

A solution of 15.30 g (11.70 mmol) of ditosylate 1 prepared from PEO of average MW 1000 in 153 ml of absolute ethanol was cooled in an ice bath, and a stream of ammonia was introduced over a period of 30 minutes. The reaction mixture was heated in a stainless steel reactor at 100° C. for 16 hr, cooled to room temperature, and then filtered. The filtrate was concentrated to remove solvent, treated with water (153 ml) and 1.0N NaOH (46.8 ml), and extracted twice with $CHCl_3$. The $CHCl_3$ extracts were dried over anhydrous magnesium sulfate, filtered and then concentrated to leave 12.20 g of product (2) ($R^2=H$).

A solution of 11.22 g (11.24 mmol) of the diamine (2) in 56 ml of DMSO was treated with triethylamine (3.13 ml, 22.5 mmol) and a solution of 4.017 g (11.24 mmol) of diethylenetriaminepentaacetic acid dianhydride in DMSO (56 ml). The reaction mixture was stirred at room temperature for 16 hr, and then treated with 448 ml of water. The resulting solution was filtered through a 0.45 μm filter and the filtrate was diafiltered against water in a diafiltration cell equipped with a 3000 MW cut-off membrane to leave 225 ml of solution.

A 208 ml portion of the aqueous solution was treated with a two-fold excess of gadolinium (III) chloride hexahydrate, and then diafiltered against water. Lyophilization of the retentate yielded 11.58 g of product (Ia, $R^2=H$) of average MW 12,500. Elemental analysis for $C_{60}H_{112}GdN_5O_{30} \cdot 2H_2O$:

| Element | % Theory | % Found |
|---------|----------|---------|
| C       | 45.70    | 45.95   |
| H       | 7.42     | 7.53    |
| N       | 4.44     | 3.85    |
| Gd      | 9.97     | 10.20   |

EXAMPLE 6

Example 5 was repeated except that the starting PEO had an average MW of 1450. The lyophilized product was determined to have an average MW of 21,900.

EXAMPLE 7

Example 1 was repeated except that B4A-dianhydride was used in place of DTPA-dianhydride. The product (Ib) was determined to have an average MW of 17,600.

Elemental analysis for $C_{88}H_{156}ClGdN_6O_{38} \cdot 4H_2O$:

| Element | % Theory | % Found |
|---------|----------|---------|
| C       | 48.69    | 48.56   |
| H       | 7.61     | 7.58    |
| N       | 3.87     | 3.76    |
| Gd      | 7.24     | 7.09    |

EXAMPLE 8

Example 1 was repeated except that P4A-dianhydride was used in place of DTPA-dianhydride. The product (Ic) was determined to have an average MW of 20,000.

Elemental analysis for $C_{83}H_{153}ClGdN_5O_{38} \cdot 4H_2O$:

| Element | % Theory | % Found |
|---------|----------|---------|
| C       | 47.61    | 47.38   |
| H       | 7.75     | 7.96    |
| N       | 3.34     | 3.21    |
| Gd      | 7.51     | 7.46    |

EXAMPLE 9

Example 1 was repeated except that $DyCl_3$ was used in place of $GdCl_3$. The lyophilized product was found to have an average MW of 14,800. The relaxivity $(T_2)^{-1}$ of this material at 20 MHZ and 40° C. was found to be 0.109 $mM^{-1}s^{-1}$. Elemental analysis for $C_{82}H_{156}DyN_5O_{40}$:

| Element | % Theory | % Found |
|---------|----------|---------|
| C | 48.89 | 48.76 |
| H | 7.80 | 7.87 |
| N | 3.48 | 3.48 |
| Dy | 8.07 | 7.80 |

EXAMPLE 10

Example 9 was repeated except that the starting PEO had an average MW of 2000. The lyophilized product was found to have an average molecular weight of 15,300. Elemental analysis for $C_{106}H_{204}DyN_5O_{52}\cdot 4H_2O$:

| Element | % Theory | % Found |
|---------|----------|---------|
| C | 48.46 | 48.71 |
| H | 8.17 | 8.05 |
| N | 2.68 | 2.52 |
| Dy | 6.21 | 6.04 |

EXAMPLE 11

Example 9 was repeated except that the starting PEO had an average MW of 3350. The lyophilized product was found to have an average molecular weight of 20,100. Elemental analysis for $C_{168}H_{328}DyN_5O_{83}\cdot H_2O$:

| Element | % Theory | % Found |
|---------|----------|---------|
| C | 51.15 | 50.93 |
| H | 8.48 | 8.45 |
| N | 1.78 | 1.80 |
| Dy | 4.12 | 4.05 |

EXAMPLE 12

Example 5 was repeated except that $DyCl_3$ was used in place of $GdCl_3$. The lyophilized product was found to have an average MW of 45,500. The relaxivity $(T_2)^{-1}$ of this material at 20 MHZ and 40° C. was found to be 0.122 $mM^{-1}s^{-1}$. Elemental analysis for $C_{80}H_{152}DyN_5O_{40}\cdot 4H_2O$:

| Element | % Theory | % Found |
|---------|----------|---------|
| C | 46.68 | 46.75 |
| H | 7.83 | 7.69 |
| N | 3.40 | 3.15 |
| Dy | 7.89 | 8.04 |

Examples 13–16 illustrate the preparation of crosslinked polymers of the invention.

EXAMPLE 13

A solution of 15.45 g (8.788 mmol) of ditosylate (1) (prepared from PEO of average MW 1450) in 155 mls of dioxane was treated with 20.4 g (0.176 mol) of 1,6-hexanediamine. The reaction mixture was heated in a stainless steel reactor at 160° C. for 16 hours. The cooled reaction mixture was concentrated to remove solvent, and then treated with water (309 ml) and 1.0N NaOH (35.2 ml). The aqueous solution was washed twice with ether, and then extracted twice with $CHCl_3$. The combined $CHCl_3$ extracts were dried over anhydrous magnesium sulfate, filtered and concentrated at 80° C. at 0.5 mm Hg to remove solvent and excess 1,6-hexanediamine and to leave 12.63 g of product (2) ($R^2=H_2N(CH_2)_6$).

A solution of 4.00 g (2.43 mmol) of (2) ($R^2=H_2N(CH_2)_6$) in 44 ml of DMSO was treated with triethylamine (1.35 ml, 9.72 mmol) and a solution of 0.867 g (2.43 mmol) of diethylenetriaminepentaacetic acid dianhydride in DMSO (48 ml). The reaction mixture was stirred at room temperature for 16 hours, and then treated with 384 ml of water. The resulting solution was filtered through a 0.45 μm nylon filter and the filtrate was diafiltered against water in a diafiltration cell equipped with a 10,000 MW cut-off membrane.

The retentate aqueous polymer solution was treated with a two-fold excess of gadolinium(III) chloride hexahydrate and then diafiltered against water as described above. Lyophilization yielded 2.10 g of cross-linked product of average MW 49,800 and containing 8.03% Gd by weight.

EXAMPLE 14

In a manner similar to Example 13, a cross-linked polymeric gadolinium chelate of average Mw 36,200 containing 9.30% Gd by weight was prepared from a solution of 3.31 g (2.01 mmol) of (2) ($R^2=-(CH_2)_6NH_2$) in 76 ml of DMSO, triethylamine (1.12 ml, 8.04 mmol) and a solution of 1.078 g (3.016 mmol) of diethylenetriaminepentaacetic acid dianhydride in DMSO (79 ml).

EXAMPLE 15

In a manner similar to Example 13, a cross-linked polymeric gadolinium chelate of average MW 95,300 containing 11.30% Gd by weight was prepared from a solution of 3.00 g (1.82 mmol) of (2) ($R^2=-(CH_2)_6NH_2$) in 69 ml of DMSO, triethylamine (1.02 ml, 7.29 mmol) and a solution of 1.303 g (3.645 mmol) of diethylenetriaminepentaacetic acid dianhydride in DMSO (72 ml). The relaxivity $(T_1)^{-1}$ of this material at 20 MHz and 40° C. was found to be 8.55 $mM^{-1}s^{-1}$.

EXAMPLE 16

In a manner similar to Example 13, ditosylate (1) (prepared from PEO of average MW 1450) was reacted with tris(2-aminoethyl) amine to yield (2) ($R^2=CH_2CH_2N(CH_2CH_2NH_2)_2$).

A cross-linked polymeric gadolinium chelate of average MW 41,400 was prepared from a solution of 0.80 g (0.47 mmol) of (2) ($R^2=CH_2CH_2N(CH_2CH_2NH_2)_2$) in 8 ml of DMSO, triethylamine (0.39 ml, 2.8 mmol) and a solution of 0.34 g (0.94 mmol) of diethylenetriaminepentaacetic acid dianhydride in DMSO (8 ml). The relaxivity $(T_1)^{-1}$ of this material at 20 MHz and 40° C. was found to be 10.2 $mM^{-1}s^{-1}$.

MR IMAGING STUDIES

The compositions of Examples 1, 2, 4, 5 and 6 were imaged in a Rabbit V-2 (carcinoma) Tumor Model as follows. The dose of each composition was adjusted to 0.1 mmol Gd per Kg, i.e., the concentrations were adjusted respectively to 102 mM, 124 mM, 49 mM, 131 mM, and 53.5 mM solutions. For each example, 3 rabbits were employed. Rabbits were anesthetized, injected and imaged on a standard magnetic resonance imaging device. Axial pre-contrast and post-contrast scans at time intervals of t=0 (immediately after injection), 15 min, 30 min, 60 min and 24 hr were made in 3 mm slices (5 mm apart) of areas from the liver to the legs. Plots of relative enhancement vs. time were derived from three regions of interest (ROI) from enhancing tumor in the right leg, three ROI from enhancing tumor in the left leg and one ROI from muscle.

Figure 1:
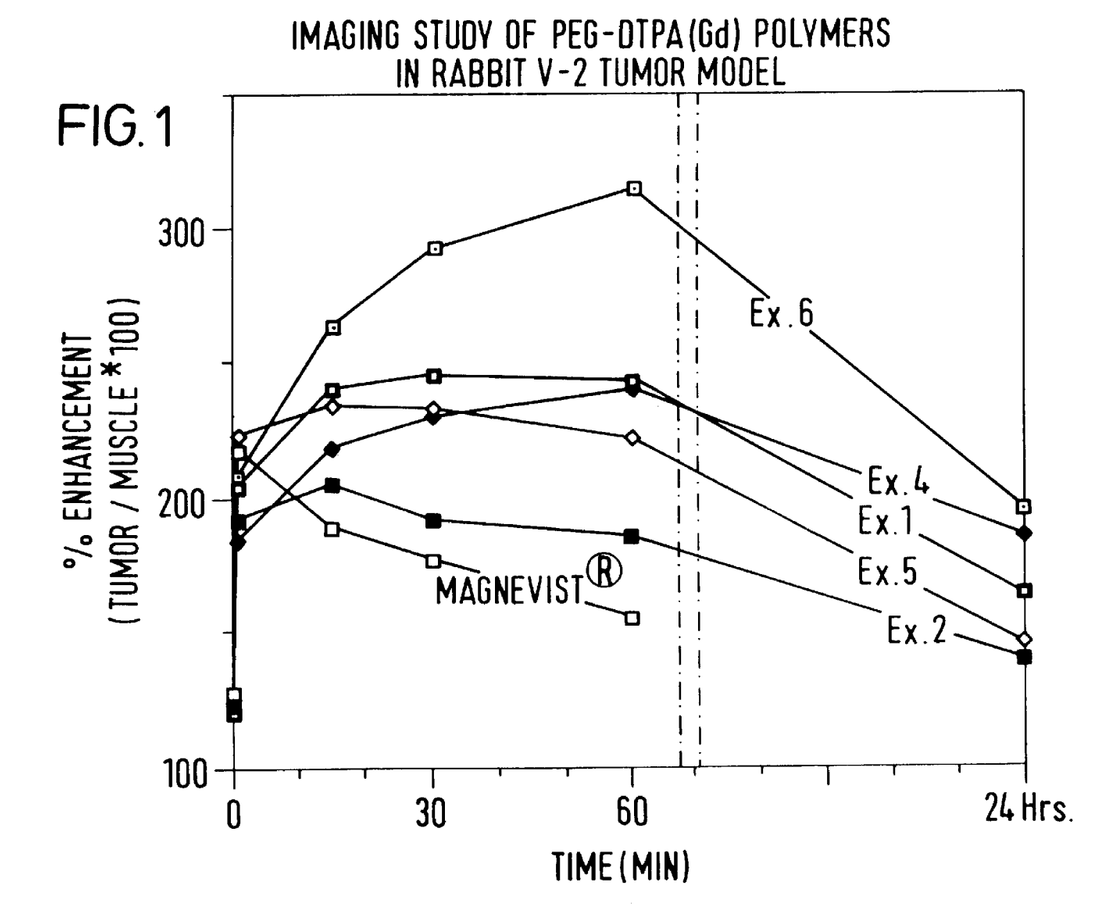
FIG. 1 is a plot of signal enhancement over time for various compositions of this invention and a prior art control in a Rabbit V-2 Tumor Model.
Figure 2:
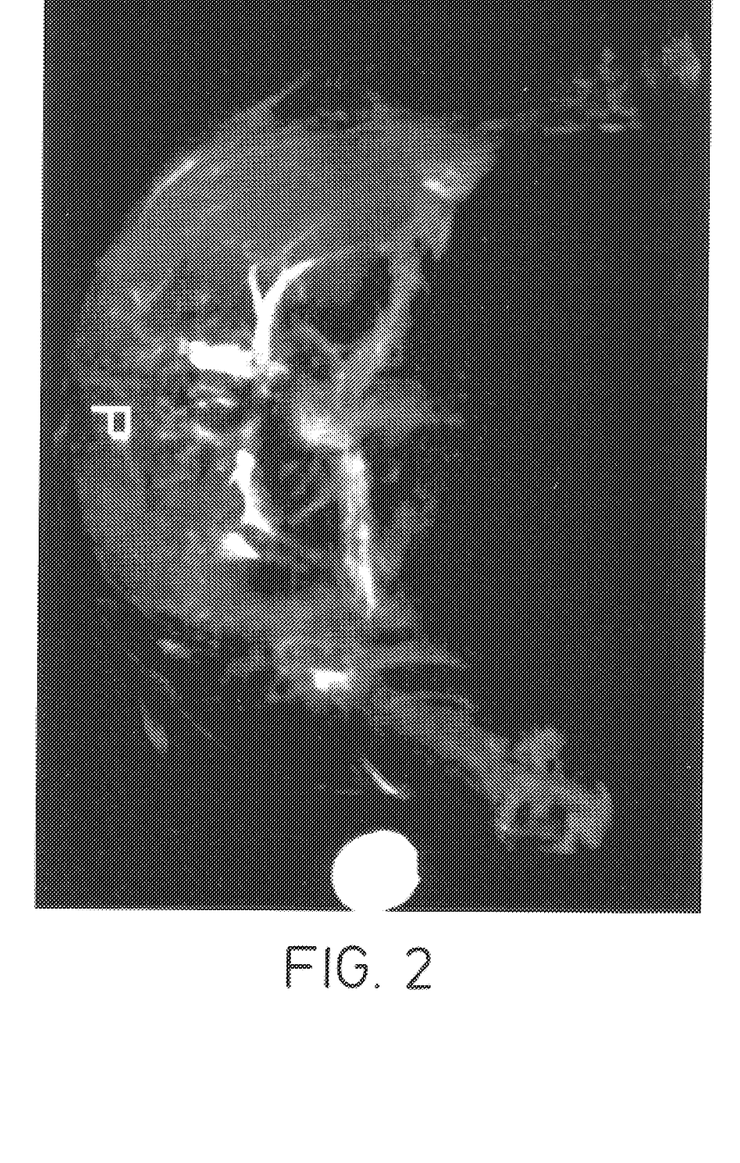
FIGS. 2 and 3 are MR images of the abdominal area of a rabbit before and after administration of a contrast enhancing composition in accordance with this invention.
Figure 3:
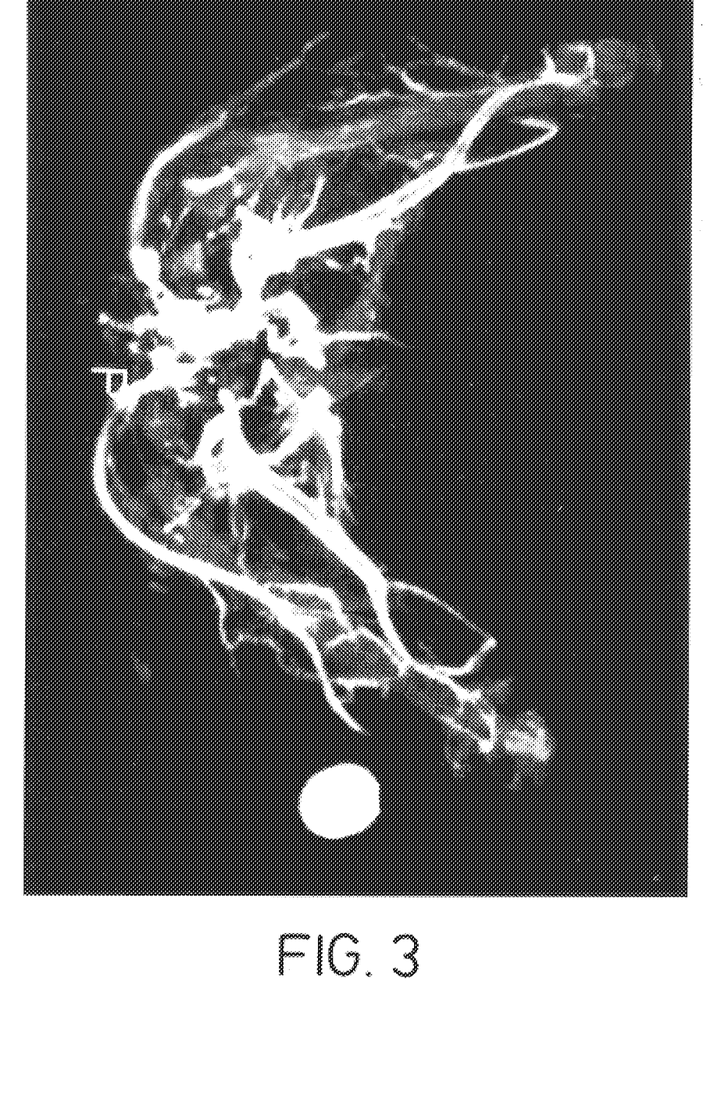

As is indicated by the plots in FIG. 1 and the images of FIGS. 2 and 3, the compositions of this invention exhibited outstanding image enhancement and dramatically improved uptake in the tumor model as compared to the Magnevist® control.

In addition to their demonstrated specificity to accumulation in tumors, the polymers of this invention are expected to be effective in imaging the spleen and blood brain barrier defects, in imaging sites of infection, and in imaging perfusion defects such as those found in ischemic tissues.

The invention has been described in detail with particular reference to certain preferred embodiments thereof, but it will be understood that variations and modifications can be effected within the spirit and scope of the invention.

We claim:

1. A polymer suitable for use in MR imaging having a backbone and comprising a plurality of polymeric repeating units, each unit providing a poly(alkylene oxide) moiety linked to a residue of DTPA in the backbone, where a plurality of said repeating units have a paramagnetic metal ion associated therewith.

2. The polymer of claim 1 wherein said residue of DTPA has a paramagnetic metal ion associated therewith.

3. The polymer of claim 1 wherein said units have the structure wherein:
Z is the residue of DTPA;
Q is a poly(alkylene oxide) moiety;
$M^{(+a)}$ is one or more cations, at least one of which is a paramagnetic ion, and having a total charge of +a;
L and $L_1$ independently represent a chemical bond or a linking group;
$E^{(b)}$ is one or more counterions having a total charge of b;
w is 0 or 1;
r is 0 or 1;
d is the total charge on the linked residue of the chelating group; and
a=d+b.

4. The polymer of claim 3 wherein $M^{(+a)}$ is a paramagnetic metal ion.

5. The polymer of claim 1 wherein said polymer comprises from 2 to 1000 of said units.

6. The polymer of claim 3 wherein Q is selected from the group consisting of a poly(ethylene oxide) moiety, a poly(propylene oxide) moiety and a poly(ethylene oxide)-co-poly(propylene oxide) moiety.

7. The polymer of claim 3 wherein $M^{(+a)}$ is selected from the group consisting of $Gd^{+3}$, $Fe^{+3}$, $Mn^{+2}$, $Mn^{+3}$, $Dy^{+3}$ and $Cr^{+3}$.

8. The polymer of claim 3 wherein L and $L_1$ independently represent amino, imido, nitrilo, imino, alkylene, carbonyl, sulfonyl, sulfinyl, ether, thioether, ester, thioester, amide, thioamide, thio, dithio, phosphate, phosphonate, urelene, thiourelene, urethane, thiourethane, an amino acid linkage or a peptide linkage.

9. The polymer of claim 3 wherein L and $L_1$ independently represent an imino or amide linkage.

10. The polymer of claim 3 wherein L and $L_1$ independently represent $L_2$ and $L_3$ independently represent a chemical bond or a linking group;
R and $R^1$ independently are H, OH, alkyl, aryl, aralkyl, alkoxy, heterocyclyl, a carboxyl group, an ester group, the residue of a chelating group or a poly(alkylene oxide) moiety.

11. The polymer of claim 1 wherein said units are recurring units having the structure wherein:
Z is the residue of DTPA;
Q is a poly(alkylene oxide) moiety,
$M^{(+a)}$ is one or more cations having a total charge of +a;
$L_2$ and $L_3$ independently represent a chemical bond or a linking group;
R and $R^1$ independently are H, OH, alkyl, aryl, halogenated aryl, aralkyl, halogenated aralkyl, alkoxy, heterocyclyl, a carboxyl group, a carboxylate group, an ester group, the residue of a chelating group or a poly(alkylene oxide) moiety;
$E^{(b)}$ is one or more counterions having a total charge of b;
w is 0 or 1;
r is 0 or 1;
d is the total charge on the residue of the chelating group, and
a=d+b.

12. The polymer of claim 11 wherein Z is the residue of DTPA, $M^{(+a)}$ is $Gd^{+3}$ or $Dy^{+3}$, $L_2$ and $L_3$ represent a chemical bond, Q is a poly(ethylene oxide) moiety of MW 250–10,000, and R and $R^1$ are H or $CH_3$.

13. The polymer according to claim 1 wherein the poly(alkylene oxide) moiety is linked to the residue of DTPA by way of an amino group.

14. A polymer according to claim 3 wherein L and $L_1$ independently represent an amino linkage.

15. A polymer according to claim 6 wherein L and $L_1$ independently represent an amino linkage.

* * * * *